United States Patent [19]

Fleck

[11] Patent Number: 5,125,906
[45] Date of Patent: Jun. 30, 1992

[54] HAND-HELD DEVICE FOR FEEDING A SPRING WIRE GUIDE

[75] Inventor: Phillip B. Fleck, Douglasville, Pa.

[73] Assignee: Arrow International Investment Corporation, Wilmington, Del.

[21] Appl. No.: 608,234

[22] Filed: Nov. 2, 1990

[51] Int. Cl.$^5$ .............................................. A61M 5/00
[52] U.S. Cl. ...................................................... 604/171
[58] Field of Search ............... 604/158, 159, 164, 171; 128/772, 657

[56] References Cited

U.S. PATENT DOCUMENTS

| 3,416,531 | 12/1968 | Edwards | 604/95 |
| 3,521,620 | 7/1970 | Cook | 128/772 |
| 3,547,103 | 12/1970 | Cook | 128/772 |
| 3,561,445 | 2/1971 | Katerndahl et al. | 604/159 |
| 3,774,605 | 11/1973 | Jewett | 604/159 |
| 3,826,256 | 7/1974 | Smith | 604/159 |
| 3,835,854 | 9/1974 | Jewett | 604/159 |
| 3,847,140 | 11/1974 | Ayella | 128/772 |
| 3,995,628 | 12/1976 | Gula et al. | 604/159 |
| 4,160,451 | 7/1979 | Chittenden | 604/159 |
| 4,274,408 | 6/1981 | Nimrod | 604/165 |
| 4,724,846 | 2/1988 | Evans, III | 128/772 |
| 4,726,369 | 2/1988 | Mar | 606/1 |
| 4,799,496 | 1/1989 | Hargreaves et al. | 128/772 |
| 4,813,938 | 3/1989 | Raulerson | 604/167 |
| 4,844,092 | 7/1989 | Rydell et al. | 128/772 |
| 4,860,757 | 8/1989 | Lynch et al. | 128/657 |

FOREIGN PATENT DOCUMENTS 207358 2/1968 U.S.S.R. .............................. 128/657

OTHER PUBLICATIONS

Certified Translation Soviet Moroz Inventor's Certificate No. 207,358.
External Jugular Vein Approach: J-Wire Technique, Blitt, et al, 1974, pp. 118-120.
Catheter Replacement of the Needle in Percutaneous Arteriography, Seldinger, 1953, pp. 368-376.
Central Venous Catheterization via the External Jugular Vein, Blitt, et al, JAMA, Aug. 12, 1974, pp. 817-818.

Primary Examiner—John J. Wilson
Assistant Examiner—Jeffrey A. Smith
Attorney, Agent, or Firm—Synnestvedt & Lechner

[57] ABSTRACT

A device for feeding a spring wire guide with a single hand. The device comprises a longitudinal having an rear end member connected to a source of spring wire guide; a second end forming a barrel with an axial bore for feeding and straightening the spring wire guide as it is fed toward syringe; a central open section separating the first and second ends and providing thumb and forefinger access to the spring wire guide; and a handle affixed to said base proximate to said central section for enabling the spring wire guide feeding apparatus to be held and supported by the middle, ring and small fingers of the administering medical professional.

6 Claims, 2 Drawing Sheets

HAND-HELD DEVICE FOR FEEDING A SPRING WIRE GUIDE

FIELD OF THE INVENTION

The present invention is directed to devices for feeding a spring wire guide into a syringe or body cavity. In particular, the present invention is directed to a device for feeding a spring wire guide into a syringe or body cavity which device can be utilized with a single hand, and which further functions to straighten the spring wire guide as it is fed.

BACKGROUND OF THE INVENTION

The Seldinger technique, developed by Sven I. Seldinger in the early 1950s, is frequently used for introducing a spring wire guide into a vein or body cavity in order to facilitate catheter placement within a vein or other body cavity. Pursuant to this technique, in its most primitive form, a hollow needle punctures a vein, is inserted and rotated 180°. A spring wire guide is then introduced into the vein or body cavity through the needle. The needle is removed, and the wire guide is held in place. The catheter is then threaded over the spring wire guide.

Blitt et al., in "Central Venous Catheterization Via the External Jugular Vein,"*Journal of the American Medical Association*, Aug. 12, 1974, pp. 817-818, expanded upon the Seldinger technique by initially introducing the needle via a syringe and by then utilizing a J-shaped guide wire to facilitate catheter insertion. In practice, following the insertion of the needle and the drawing of venal blood, the syringe is detached from the needle and the spring or "J" wire guide inserted through the needle.

More recently, several devices have been developed which combine the wire guide and syringe injection functions, such as disclosed in U.S. Pat. No. 4,274,408 to Nimrod, and U.S. Pat. No. 4,813,938 to Raulerson. Such devices comprise highly specialized and complex syringes, containing central apertures for the wire guide. The main advantage of such syringes is that they minimize bleeding during the insertion of the wire guide. The present invention, in its preferred embodiment, is directed toward feeding a guide wire into such syringes.

There are several prior art devices for introducing the spring wire guide into the needle or syringe. These devices typically require the use of two hands by the administering medical professional. The required need for two hands makes the introduction of the spring wire guide cumbersome, particularly when used with syringes such as those disclosed in U.S. Pat. Nos. 4,274,408 and 4,813,938.

U.S. Pat. No. 4,713,059 to Bickelhaupt discloses such a device which must be supported by both hands of the physician or administering medical professional. As can be seen in FIGS. 5 and 6 of U.S. Pat. No. 4,713,059, the device is held by two hands and the wire probe is advanced, by the administering medical professional, by shuttling his or her fingers back and forth.

A particular problem which may arise during the introduction of the spring wire guide, sometimes referred to as "J" wire, is that the tip may tend to fold back upon itself. Once in the vein or body cavity, the vein or body cavity tends to keep the wire tip straight, but the tendency for it to assume its set position may hinder the advancement of the wire as it is moved around and turns and bends in the vessel, and in particular as it progresses through the chambers of the heart in cardiac catheterization applications.

In view of the above, it would be desirable to have a spring wire guide feed device which can be utilized with a single hand of the administering professional and which further functions to straighten the spring wire guide as it is fed into a syringe.

It is therefore an object of the present invention to provide a spring wire guide feeding device which facilitates the feeding of the spring wire guide with only one hand by the administering medical professional, and thus freeing the professional's other hand to maneuver or control the introducer needle or syringe.

It is still a further object of the present invention to provide a spring wire guide feeding device which further provides means for straightening the end or tip of the spring wire guide as it fed through the device.

It is still a further object of the present invention to provide a spring wire guide feeding apparatus which is compact and in which the spring wire guide feed tube can be attached to the handle of the feeding device.

It is yet a further object of the present invention to provide a spring wire guide feeding apparatus which minimizes the possibility of contamination.

Accordingly, the present invention is thus directed to the combination of a straightening tube and hand-held feed device which supports and feeds a spring wire guide. The device of the present invention is held and supported in a single hand of the administering medical professional. The device of the present invention permits the spring wire guide to be held and advanced between the thumb and forefinger of the administering medical professional, through a straightening bore, and then through the syringe plunger, and into the vein or body cavity.

SUMMARY OF THE INVENTION

In accordance with the present invention, a hand-held spring wire guide feeding apparatus is disclosed. The disclosed apparatus comprises a longitudinal base member having an attached first end member for feeding a spring wire guide, a second end forming a barrel and having an axial bore for receiving and straightening said spring wire guide fed from said first end member, a central open section situated between said first and second ends for providing finger access to said spring wire guide so as to advance said spring wire guide between said first and second ends; and a handle affixed to the underside of said base proximate to said central open section for holding and supporting said spring wire guide feeding apparatus. The disclosed device is thus designed to be held and operated with one hand by the administering medical professional, leaving the other hand free to position the introducer needle or syringe.

DETAILED DESCRIPTION OF THE PRESENT INVENTION

Figure 1:
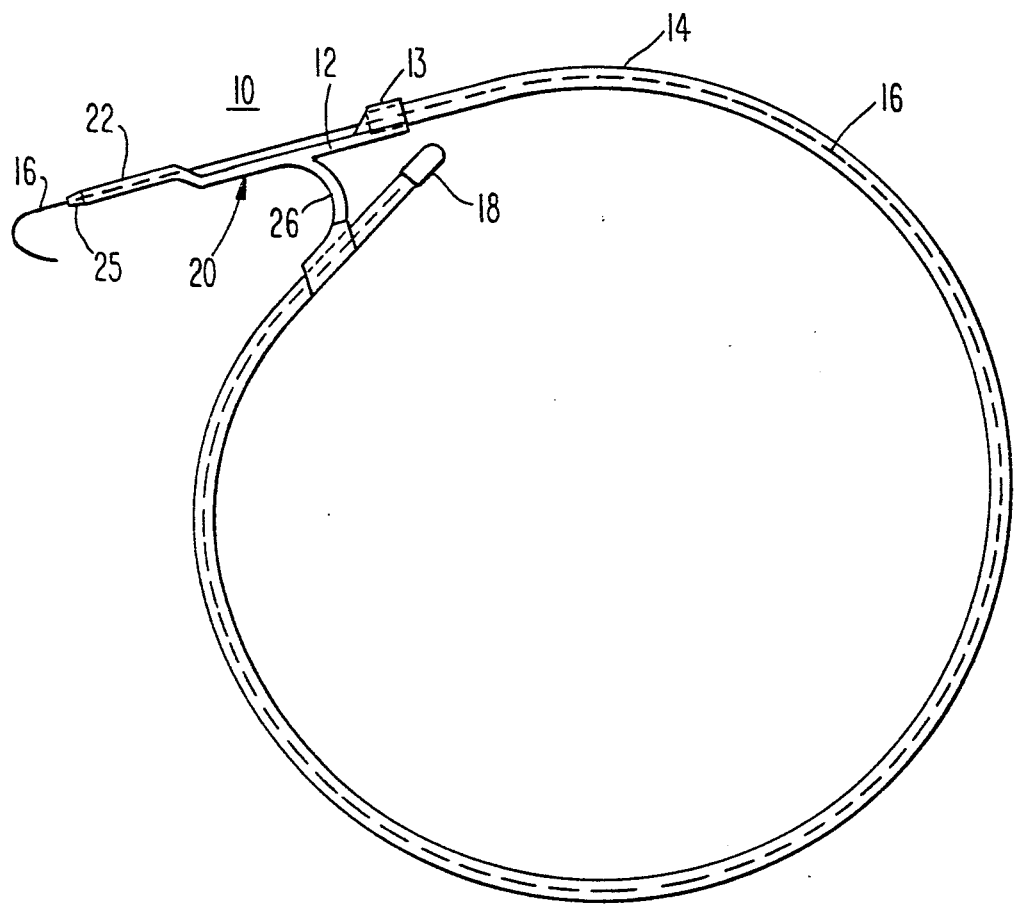
FIG. 1 is a perspective view of the spring wire guide feeding mechanism of the present invention.

The present invention is described with reference to the enclosed Figures wherein the same numbers are utilized where applicable. Referring to FIGS. 1-5, the spring wire guide feeding mechanism 10 of the present invention is shown. The device will preferably be constructed from a molded plastic. As can be seen, the device comprises a longitudinal base member 12. The longitudinal base member 12 includes an attached elevated rear end member 13 which fastens to and attaches a flexible tube 14. Flexible tube 14 houses a coiled spring wire guide 16 (represented by the broken lines of FIG. 1). The coil spring wire guide 16 is introduced into the flexible tube 14 by removing stopper 18.

The central section 20 of the longitudinally extending member is open and attaches to an elevated barrel member 22. The barrel member 22 includes an axial bore 24, shown most particularly in FIGS. 3 and 4, which permits the spring wire guide 16 to be fed through and straightened. The elevation of the barrel 22 and rear end member 13 suspend the spring wire guide within the central open section 20, and thus facilitate its access to the thumb and forefinger of the medical professional administering the catheterization. Preferably, the barrel member has a tapered distal end portion 25. The tapered distal end portion 25 facilitates connection to the introducer needle or syringe, and the feeding of the wire guide 16.

The device 10 further includes an arced handle member 26 attached to the underside of longitudinal base member 12. The arced handle member 26 cups the middle, ring, and small fingers of the medical professional administering the catheterization. The arced handle member 26 includes a forward beveled U-shaped clamp 28, which as most particularly shown in FIGS. 1, 3, 4 and 5, facilitates the attachment of flexible tube 16 to the arced handle member 26.

Figure 2:
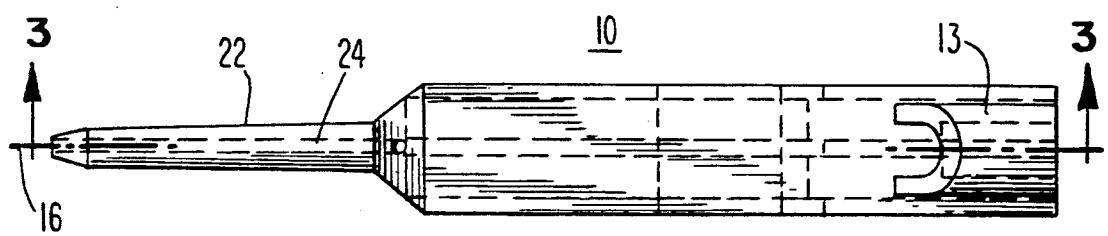
FIG. 2 is a overhead plan view of the longitudinal base and barrel for the spring wire guide feeding apparatus of the present invention.
Figure 3:
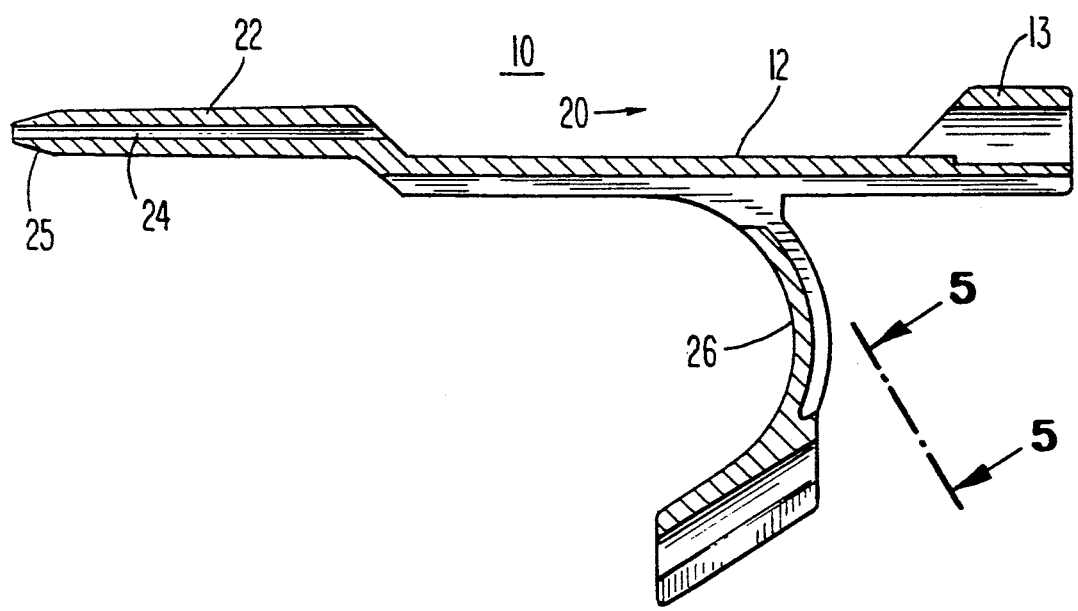
FIG. 3 is a section view of the handle of the spring wire guide feeding mechanism along line 3—3 of FIG. 2.
Figures 4, 5:
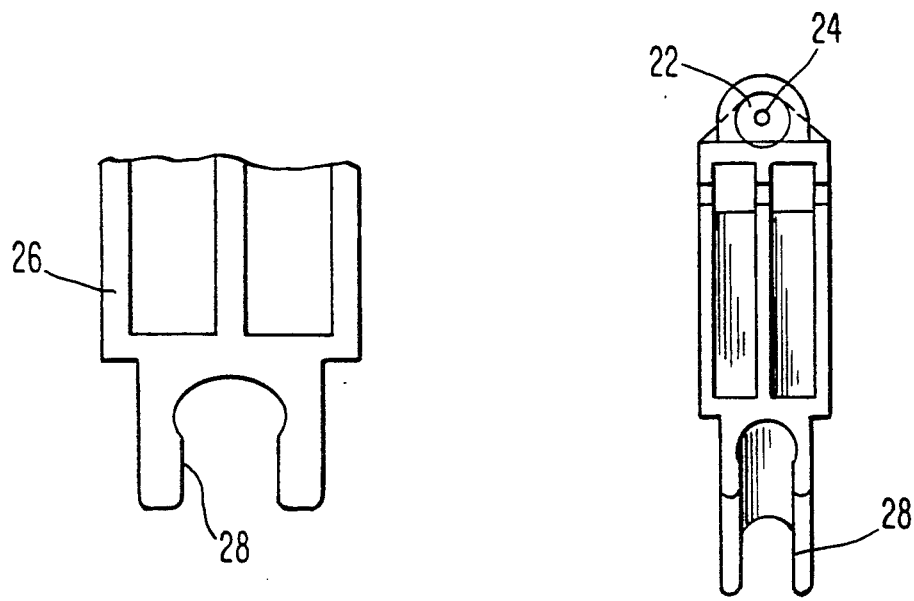
FIG. 4 is a rear perspective view of the spring wire guide feeding mechanism of the present invention.
FIG. 5 is an isolated view of the U-shaped clamping mechanism of the spring wire guide of the present invention along line 5—5 of FIG. 3.

FIG. 2 is a plan view of the handle 26 and barrel member 22 of the present invention. As can be seen, the spring wire guide is fed from tube 14 through the elevated rear member 13, through the central open section which extends over the longitudinal member 12 and through the axial bore 24 of barrel 22.

The operation of the present invention is now described with reference to the enclosed Figures. Referring to FIG. 1, a spring wire guide 16 may be initially fed through the flexible tube 14 via an opening created by the removal of stopper 18. The flexible tube 14 is then connected to the spring wire guide feed device at the attached elevated rear end member 13. The wire 16 is then fed forward over the open section 20 and into the axial bore 24 of barrel 22 where the wire 16 is straightened. The flexible holding tube 14 is then bent around and secured to the forward beveled U-shaped clamp 28 located at the base of the arced handle member 26. The elevation of the barrel 22 and rear end member 13 effectively suspend the wire 16 with the open section thus facilitating thumb and forefinger access by the administering medical professional. Typically, the assembly with flexible tube 14 and wire guide in place, as just described, is provided by the manufacturer to the end user in a sterile package along with other components useful for the catheterization of a blood vessel.

The device is held and supported at the arced handle member 26 by the middle, ring, and small fingers of the gloved medical professional introducing the spring wire guide. The medical professional will typically be wearing a sterile glove. The gloved thumb and forefinger of the medical professional are then used to advance or retract the suspended spring wire guide 16 at open section 20. Although the spring wire guide may then be introduced directly through a hollow needle or an introducer catheter, it is most preferably then fed through an opening in the proximal end of the plunger of a syringe such as that disclosed in U.S. Pat. Nos. 4,272,408 and 4,813,938. Use of the device allows for the advancement of the wire guide with one hand, leaving the other hand free for use in positioning the syringe. Because only a small portion of wire guide 16 is exposed to the outside air and the two fingers of the gloved administering professional, use of the device minimizes risk of contamination of the wire guide during the insertion procedure.

While the present invention has been described with reference to the above discussed enclosed preferred embodiment, it is to be appreciated that other embodiments fulfill the scope of the present invention and that the present invention should be construed with reference to the claims attached hereto.

What is claimed is:

1. A hand-held spring wire guide feeding apparatus comprising:
   a longitudinal base having an attached rear end having an opening for feeding a spring wire guide;
   a flexible tube for holding a spring wire guide and having a proximal end attached to said attached rear end,
   said longitudinal base having a forward end forming a barrel having a coaxially extending bore for receiving and straightening said spring wire guide as it is fed from said rear end, and terminating in a tapered distal portion,
   a central open section separating said rear and forward ends for providing finger access to said spring wire guide so as to advance said spring wire guide between said rear end means and said forward end; and
   a handle affixed to the underside of said longitudinal base proximate to said central open section for holding and supporting said wire guide feeding apparatus, said handle having an arcuate surface configured to cup the fingers of the user and further having a clamp for securing a distal end of said flexible tube to said handle.

2. The hand-held spring wire guide feeding apparatus of claim 1 wherein said clamp is U-shaped.

3. The hand-held spring wire guide feeding apparatus of claim 1 wherein said handle having an arcuate surface extends downwardly and forwardly forming a curved surface path so as to cup the fingers of the user, thereby providing support for the apparatus during advancement of the wire guide.

4. The hand-held spring wire guide feeding apparatus of claim 3 wherein said clamp extends generally rearwardly of said curved surface for securing the distal end portion of said flexible tube thereto.

5. A hand held spring wire guide feeding apparatus comprising:
   a longitudinal base member having an elevated first end member attached thereto, said first end member having an axially extending guide passageway;

an elongated flexible tubular spring wire guide housing, said elongated flexible tubular housing having a proximal end portion attached to said first end member for interconnecting the elongated flexible tubular housing with the axially extending guide passageway, said elongated flexible tubular housing further having a distal end portion having a sealing stopper for protecting a spring wire guide within the housing from airborne contaminants, said base member having a second end member forming a barrel having an axial bore for receiving and straightening said spring wire from said elongated flexible tubular spring wire guide housing through the passageway in said first end member, said elongated flexible tubular housing being in alignment with the passageway in said first end member;

a central open, rigid, section separating said first and second end members providing unrestricted access to said spring wire guide so as to allow for advancement of said guide so as to advance said guide lengthwise of said platform and said first and second end members; and an arced handle affixed to the underside of said base member proximate to said central open platform section, said handle extending downwardly and forwardly forming a curved surface path which cups the fingers of the user thereby providing support for the apparatus during advancement of the wire guide, said handle having a clamp extending generally rearwardly of said curved surface for securing the proximal end portion of said flexible tube thereto.

6. A hand-held spring wire guide feeding apparatus comprising:

a longitudinal base having an attached first rear end member having an axial bore for receiving a spring wire guide;

a flexible tube for housing said spring wire guide, said flexible tube having a proximal end port interconnected with said axial bore, said longitudinal base having a second end member forming an elevated barrel having an axial bore for receiving and straightening said spring wire guide as said wire guide is fed from said attached rear end member, each of said bores being in substantial axial alignment;

a central open section separating said first rear end member and said second members for providing unrestricted access to said spring wire guide so as to allow for the advancement of said spring wire guide between said first and second end members; and an acred handle affixed to the underside of said base proximate to said central open section said handle being configured to cup the fingers of the hand of the user for holding and supporting said elongated base member, said handle having a U-shaped clamp for securing said flexible tube to said handle.

* * * * *